(12) United States Patent
Tamor et al.

(10) Patent No.: US 9,862,853 B2
(45) Date of Patent: Jan. 9, 2018

(54) DISPERSION, GEL AND EMULSIFICATION SYSTEM

(75) Inventors: Mildred Estrada Tamor, Singapore (SG); David Peter Dowdell, Glenfield (AU)

(73) Assignee: CRODA SINGAPORE PTE LIMITED, Singapore (SG)

( * ) Notice: Subject to any disclaimer, the term of this patent is extended or adjusted under 35 U.S.C. 154(b) by 0 days.

(21) Appl. No.: 12/450,097

(22) PCT Filed: Mar. 11, 2008

(86) PCT No.: PCT/AU2008/000320
§ 371 (c)(1),
(2), (4) Date: Feb. 19, 2010

(87) PCT Pub. No.: WO2008/109935
PCT Pub. Date: Sep. 18, 2008

(65) Prior Publication Data
US 2010/0150850 A1 Jun. 17, 2010

(30) Foreign Application Priority Data
Mar. 12, 2007 (GB) .................................. 0704709.5

(51) Int. Cl.
| | | |
|---|---|---|
| A61K 47/30 | (2006.01) | |
| A61K 8/73 | (2006.01) | |
| A61Q 17/04 | (2006.01) | |
| A61Q 19/10 | (2006.01) | |
| A61Q 1/14 | (2006.01) | |
| C09D 133/02 | (2006.01) | |
| A61K 8/02 | (2006.01) | |
| A61K 8/04 | (2006.01) | |
| A61K 8/81 | (2006.01) | |
| A61Q 5/02 | (2006.01) | |
| A61Q 5/12 | (2006.01) | |
| A61Q 19/00 | (2006.01) | |
| B01F 17/00 | (2006.01) | |
| C08F 20/00 | (2006.01) | |
| A61K 8/37 | (2006.01) | |
| A61Q 19/02 | (2006.01) | |
| A61Q 19/08 | (2006.01) | |

(52) U.S. Cl.
CPC .......... *C09D 133/02* (2013.01); *A61K 8/0208* (2013.01); *A61K 8/042* (2013.01); *A61K 8/375* (2013.01); *A61K 8/8147* (2013.01); *A61Q 5/02* (2013.01); *A61Q 5/12* (2013.01); *A61Q 19/00* (2013.01); *B01F 17/0021* (2013.01); *B01F 17/0028* (2013.01); *C08F 20/00* (2013.01); *A61K 2800/48* (2013.01); *A61Q 1/14* (2013.01); *A61Q 17/04* (2013.01); *A61Q 19/02* (2013.01); *A61Q 19/08* (2013.01)

(58) Field of Classification Search
CPC ...... A61K 2800/48; A61K 8/04; A61K 8/042; A61K 8/362; A61K 8/8147

USPC ................ 424/59, 70.11; 510/119, 136
See application file for complete search history.

(56) References Cited

U.S. PATENT DOCUMENTS

| | | | | |
|---|---|---|---|---|
| 4,038,048 | A * | 7/1977 | Thrower, Jr. | ......... B24B 37/044 51/298 |
| 4,234,599 | A * | 11/1980 | Van Scott et al. | ............. 514/451 |
| 4,299,755 | A * | 11/1981 | Keggenhoff et al. | ........... 524/55 |
| 4,368,189 | A | 1/1983 | Mentlik | |
| 4,664,909 | A * | 5/1987 | Marschner | ...................... 424/65 |
| 4,683,134 | A * | 7/1987 | Palinczar | ................. A61K 8/34 424/59 |
| 5,455,025 | A * | 10/1995 | Pereira et al. | ................... 424/59 |
| 5,585,104 | A | 12/1996 | Ha et al. | |
| 5,798,108 | A | 8/1998 | Nadaud et al. | |
| 5,846,454 | A | 12/1998 | Koczo et al. | |
| 5,858,406 | A * | 1/1999 | Stead et al. | .................... 424/465 |
| 5,945,095 | A | 8/1999 | Mougin et al. | |
| 6,200,596 | B1 | 3/2001 | Schwartzmiller et al. | |
| 6,294,192 | B1 * | 9/2001 | Patel et al. | ..................... 424/451 |
| 6,365,656 | B1 * | 4/2002 | Green et al. | .................. 524/313 |
| 7,108,860 | B2 * | 9/2006 | Dueva et al. | ............... 424/401 |
| 2004/0089195 | A1 | 5/2004 | Moodycliffe et al. | |
| 2005/0095210 | A1 | 5/2005 | Mattai et al. | |
| 2005/0136098 | A1 | 6/2005 | Spadini et al. | |
| 2006/0051486 | A1 * | 3/2006 | Dowdell et al. | .............. 426/601 |

FOREIGN PATENT DOCUMENTS

| | | |
|---|---|---|
| JP | 2000-516614 | 12/2000 |
| WO | WO 1998/006438 | 2/1998 |
| WO | WO 1998/023150 | 4/1998 |
| WO | WO 2000/040212 | 7/2000 |
| WO | WO 2000/061077 | 10/2000 |
| WO | WO 2001/015659 | 3/2001 |
| WO | WO 2005/011567 | 2/2005 |
| WO | WO 2005/097834 | 10/2005 |
| WO | WO 2006/000059 | 1/2006 |

OTHER PUBLICATIONS

Gaonkar (Journal of the American Oil Chemists' society, vol. 66, No. 8, Published Aug. 1989, p. 1090-1092).*
International Search Report dated May 17, 2008 for PCT/AU2008/000320.
Official Action dated Sep. 1, 2013 in corresponding Japanese Application No. 2009-552971 (English translation provided).

* cited by examiner

*Primary Examiner* — Alma Pipic
(74) *Attorney, Agent, or Firm* — RatnerPrestia

(57) ABSTRACT

A dispersion which contains particles of a carboxylic acid polymer dispersed in an organic medium containing an emollient ester and/or a non-ionic surfactant. The dispersion can be used to form a gel composition by mixing with a water miscible emollient ester and optionally water. The dispersion and gel can be used to form an emulsification system. The dispersion, gel and emulsification system are suitable for use in forming end-use emulsions, preferably at low temperature and low shear, and in particular, emulsions having a high oil phase concentration. The emulsions can be used in a wide range of applications, including personal care, household and industrial.

6 Claims, No Drawings

DISPERSION, GEL AND EMULSIFICATION SYSTEM

CROSS REFERENCE TO RELATED APPLICATION

This application is the National Phase application of International Application No. PCT/AU2008/000320, filed Mar. 11, 2008, which designates the United States and was published in English. The related International application, in its entirety, is incorporated herein by reference.

FIELD OF INVENTION

The present invention relates to a dispersion comprising a carboxylic acid polymer, to the use thereof in forming a gel composition and an emulsification system, and in particular to the use of the dispersion, gel and emulsification system in forming emulsions.

BACKGROUND

Oil-in-water and water-in-oil emulsions are widely used in the personal care and cosmetic industry to deliver ingredients to skin and hair, either by direct application thereto of milks, lotions or creams, or through the medium of wet wipes and other similar applicators.

Personal care emulsion products such as creams and milks desirably have a number of properties in combination: stability in manufacture, formulation, storage and use; a viscosity appropriate to the end use; and preferably a desirable body and good skin feel. Body and skin feel are usually assessed subjectively, and although good body and/or skin feel are commonly associated with a non-Newtonian, shear thinning viscosity profile, a shear thinning profile does not guarantee a good body or skin feel.

Emulsions also find a wider use in other applications such as industrial, e.g. in explosives, and household applications such as polishes, for example shoe polish and furniture polish, and car (or other vehicle) waxes and polishes, for example car waxes and tyre shine products.

Thickeners have been used as emulsion stabilisers. The mechanism of stabilisation when such thickeners are used appears to be that the thickener modifies the rheology of the system by increasing the low shear viscosity of the emulsion sufficiently to provide a barrier to emulsion droplet coalescence, probably by limiting the movement of the droplets.

One particular type of thickener is a high molecular weight hydrophilic carboxylic acid polymer such as the polyacrylic CARBOMER type, which, in particulate powder form, has to be dispersed homogeneously within the emulsification system. It is necessary to firstly obtain a substantially homogeneous dispersion of the polymer particles in the emulsion; and secondly to maintain the stability of the emulsion. To function effectively, the polymeric particles need to be wetted thoroughly to enable the polymer chains to untangle and become dispersed or solubilised in the aqueous phase of the emulsion. These polymers tend to clump when added to the oil or even the aqueous phase of an emulsion. The surface of a clump solvates to form a tough outer layer which prevents complete wetting of the interior of the polymer particles. This can lead to excessive mixing and wet out times, grainy texture, reduced viscosity and stability, less robust gel formation, inferior skin feel including tackiness, and partly wetted agglomerates of particles with a jelly-like appearance similar to fish eyes.

Thus, there is a need for these high molecular weight hydrophilic polymers to be included in a system which enables improved incorporation into end-use emulsions or formulated products.

SUMMARY OF THE INVENTION

We have now surprisingly discovered a dispersion, gel composition and emulsification system, which overcomes or significantly reduces at least one of the aforementioned problems.

Accordingly, the present invention provides a dispersion comprising particles of a carboxylic acid polymer dispersed in an organic medium comprising an emollient ester and/or a non-ionic surfactant.

The invention also provides a method of forming a dispersion which comprises mixing together particles of a carboxylic acid polymer, an organic medium, and an emollient ester and/or a non-ionic surfactant.

The invention further provides a gel composition comprising (i) optionally water, (ii) an organic medium, (iii) a water miscible emollient ester and/or a non-ionic surfactant having a HLB value of greater than or equal to 8, (iv) an emollient ester miscible in the organic medium and/or a non-ionic surfactant, and (v) a carboxylic acid polymer.

The invention yet further provides a method of forming a gel which comprises mixing together particles of a carboxylic acid polymer, optionally water, an organic medium, a water miscible emollient ester and/or a non-ionic surfactant having a HLB value of greater than or equal to 8, and an emollient ester miscible in the organic medium and/or a non-ionic surfactant.

The invention still further provides an emulsification system comprising (i) water, (ii) an oil, (iii) a non-ionic surfactant, (iv) optionally a water miscible emollient ester, and (v) a carboxylic acid polymer.

The invention still further provides an emulsion which is formed from (a) a dispersion comprising particles of a carboxylic acid polymer dispersed in an organic medium comprising an emollient ester and/or a non-ionic surfactant; and/or (b) a gel composition comprising (i) optionally water, (ii) an organic medium, (iii) a water miscible emollient ester and/or a non-ionic surfactant having a HLB value of greater than or equal to 8, (iv) an emollient ester miscible in the organic medium and/or a non-ionic surfactant, and (v) a carboxylic acid polymer; and/or (c) an emulsification system comprising (i) water, (ii) an oil, (iii) a non-ionic surfactant, (iv) optionally a water miscible emollient ester, and (v) a carboxylic acid polymer.

The invention still further provides the use of (a) a dispersion comprising particles of a carboxylic acid polymer dispersed in an organic medium comprising an emollient ester and/or a non-ionic surfactant; and/or (b) a gel composition comprising (i) optionally water, (ii) an organic medium, (iii) a water miscible emollient ester and/or a non-ionic surfactant having a HLB value of greater than or equal to 8, (iv) an emollient ester miscible in the organic medium and/or a non-ionic surfactant, and (v) a carboxylic acid polymer; and/or (c) an emulsification system comprising (i) water, (ii) an oil, (iii) a non-ionic surfactant, (iv) optionally a water miscible emollient ester, and (v) a carboxylic acid polymer; to form an emulsion having at least one of reduced grainy texture, improved viscosity, improved stability, more robust gel formation, improved skin feel including less tackiness, and/or reduction in "fish eyes", compared to an equivalent emulsion obtained by directly adding the carboxylic acid polymer in particulate powder form to the water and/or oil phase during formation of the emulsion.

The carboxylic acid polymer may be formed into a dispersion in any suitable liquid organic medium continuous phase. By dispersion is meant a true dispersion, i.e. where the polymer particles are stable to aggregation. The polymer is substantially homogeneously dispersed and resistant to agglomeration or settling out on standing; however, if some settling out does occur, the particles can be easily re-dispersed by simple agitation.

The dispersions according to the present invention are suitably stable, measured as described herein, preferably for greater than one month, more preferably greater than two months, particularly greater than three months, and especially greater than four months at 5° C., and/or at ambient temperature (23° C.), and/or at 43° C. The stability at even higher temperatures can also be important, and therefore the dispersions according to the invention are preferably stable, measured as described herein, suitably for greater than one week, preferably greater than two weeks, more preferably greater than 3 weeks, particularly greater than one month, and especially greater than two months at 50° C.

The stable dispersion preferably comprises in the range from 20 to 60%, more preferably 30 to 50% by weight of a carboxylic add polymer, and in the range from 40 to 80%, more preferably 50 to 70% by weight of a liquid phase, said carboxylic acid polymer being substantially homogeneously dispersed in said liquid phase which comprises an organic medium comprising an emollient ester and/or a non-ionic surfactant.

In a preferred embodiment, the dispersion according to the invention is substantially anhydrous. The term "anhydrous" as used in this specification means dispersions containing less than 10%, preferably less than 5% water by weight based on the weight of the dispersion. More preferably, the dispersions are substantially water free, i.e. contain less than 2%, particularly less than 1% water by weight. However, it will be appreciated that components of the dispersion may contain small amounts of residual water (moisture) which will be present in the dispersion.

The carboxylic acid polymers used in the dispersion of the present invention are preferably high molecular weight synthetic polycarboxy or polycarboxylic acid polymers, particularly homopolymers of acrylic acid and copolymers comprising acrylic acid and alkyl acrylates, which may be cross-linked.

The carboxylic acid polymers are hydrophilic polymers, suitably having a molecular weight of greater than 500, preferably greater than 1,000, more preferably greater than 10,000, particularly in the range from 40,000 to 3,000,000, and especially 75,000 to 2,500,000. The molecular weight of these polymers, particularly when cross-linked, can be difficult to measure, but may be determined by intrinsic viscosity. If necessary, theoretical intrinsic viscosity determinations may be employed.

The carboxylic acid polymers are generally supplied in the form of a fine white powder having a low water content (e.g. below 5% by weight) in the form of a tightly coiled molecule. The polymers are generally dispersible, but they do not tend to dissolve in water or aqueous medium, although the molecules of the polymer will uncoil when properly wetted. In use, it is usual to convert the acid to the salt by neutralisation with a suitable base. The action of neutralisation creates positive charges along the polymer chain causing charge repulsion and the swelling of the polymer. Swelling creates a gel structure through entanglement of the swollen molecules, and "structuring" of the aqueous phase, leading to highly efficient thickening, stabilising and suspension characteristics.

Preferred carboxylic acid polymers can be classified into three distinct categories, which can be roughly determined by the INCI designation and Noveon materials tradename. Suitable polymers can be selected from any materials assigned the INCI designation of CARBOMER or Acrylates\C10-30 Alkyl Acrylate Crosspolymer. Examples include materials sold under the tradenames ACRITAMER, CARBOPOL, CARBOPOL ETD, CARBOPOL ULTREZ, PEMULEN, AQUAPEC, JUNLON, POLYGEL, SYNTHALEN, and TEGO CARBOMER.

The first category have the INCI designation CARBOMER, and are marketed under various tradenames by a wide variety of companies, including the CARBOPOL range from Noveon. CARBOMERS are polymers of an unsaturated carboxylic acid containing 3 to 5 carbon atoms and less than 5% of a suitable crosslinker, preferably selected from polyalkenyl polyethers of polhydric alcohols, synthesised in a suitable organic solvent, preferably selected from acetone or lower alkyl acetates, or mixtures thereof. More specifically, CARBOMERS are homopolymers of acrylic acid crosslinked with an allyl ether of pentaerythritol, sucrose, or propylene. One particularly preferred material is OPTA-SENSE G40 CARBOMER (polyacrylic acid, ex Croda).

The second category have the INCI designation of Acrylates\C10-30 Alkyl Acrylate Crosspolymer. These materials are marketed under a range of tradenames from a number of companies, including the CARBOPOL ETD and ULTREZ ranges from Noveon. Acrylates/C10-30 Alkyl Acrylate Crosspolymers are copolymers of C10-30 alkyl acrylates and one or more monomers of acrylic acid, methacrylic acid or simple esters thereof crosslinked with an allyl ether of sucrose or pentaerythritol. The designation "10-30" refers to 10 to 30 carbon atoms. These polymers preferably comprise at least 85% of an unsaturated carboxyl monomer of 3 to 5 carbon atoms, more preferably carboxylic acids, and up to 15% of a comonomer, synthesised in an organic solvent selected from suitable ketones, esters, ethers and alcohols or mixtures thereof, more preferably mixtures of ethyl acetate and cyclohexane. One mode of action and use for these polymers is similar to that described for CARBOMERS above, i.e. chain entanglement. However the presence of hydrophobic moieties along the polymer chain allows for association of the hydrophobic groups with themselves and other hydrophobic particles, species and oils, bringing additional stability and formulation flexibility.

The third category covers a range of polymers also carrying the INCI designation Acrylates\C10-30 Alkyl Acrylate Crosspolymer, but provide increased benefits in high-electrolyte aqueous systems and emulsification, whether acting as a primary or secondary emulsifier. The most notable supplier of these materials is Noveon under the Pemulen tradename, although they are supplied by others. These materials are crosslinked copolymers of unsaturated carboxylic acid, a hydrophobic monomer, a hydrophobic chain transfer agent, and a cross-linker. The mechanism of thickening is very similar to the second category above, except that the degree of hydrophobic moieties is higher, therefore allowing for additional stability in the presence of hydrophobic groups, and additional formulation flexibility.

A particularly surprising feature of the present invention is that dispersions can be produced comprising carboxylic acid polymer at a concentration suitably greater than 5%, preferably greater than 10%, more preferably in the range from 20 to 60%, particularly 25 to 50%, and especially 30 to 40% by weight based on the total weight of the dispersion. Typically, dispersions according to the invention contain about 30% or 40% by weight of carboxylic acid polymer.

Cosmetically acceptable materials are preferred as the organic medium continuous phase, for example an oil of the type widely used in personal care or cosmetic products, such as those registered as solvents by the Cosmetics Toiletries and Fragrance Association. The organic medium preferably comprises, consists essentially of, or consists of as major component or substrate one or more oily materials which are liquid at ambient temperature, such as those selected from the group consisting of fatty alcohols, glycols, glyceride oils, vegetable oils, ester oils, fatty alcohol alkoxylates, alkyl carbonates, mineral oils and silicone oils, and mixtures thereof. Suitable silicone oils or siloxane fluids include a cyclic oligomeric dialkylsiloxane, such as the cyclic pentamer of dimethylsiloxane known as cyclomethicone. Alternative siloxane fluids include dimethylsiloxane linear oligomers or polymers having a suitable fluidity and phenyltris(trimethylsiloxy)silane (also known as phenyltrimethicone).

Specific examples of suitable organic media substrates include avocado oil, C12-15 alkyl benzoate, C12-15 alkyl ethylhexanoate, C12-15 alkyl lactate, C12-15 alkyl salicylate, C13-14 isoparaffin, C18-36 acid glycol ester, C18-36 acid triglyceride, caprylic/capric glycerides, caprylic/capric triglyceride, caprylic/capric/lauric triglyceride, caprylic/capric/linoleic triglyceride, caprylic/capric/myristic/stearic triglyceride, caprylic/capric/stearic triglyceride, castor oil, castor oil-silicone ester, cetearyl ethylhexanoate, cetearyl isononanoate, cetearyl palmitate, cetearyl stearate, cetyl dimethicone, cetyl dimethicone copolyol, cetyl ethylhexanoate, cetyl glycol isostearate, cetyl isononanoate, cetyl lactate, cetyl myristate, cetyl oleate, cetyl palmitate, cetyl ricinoleate, cetyl stearate, cocoglycerides, coconut oil, cyclomethicone, cyclopentasiloxane, cyclotetrasiloxane, decyl isostearate, decyl oleate, decyl polyglucoside, dibutyl adipate, diethylhexyl dimer dilinoleate, diethylhexyl malate, diisopropyl adipate, diisopropyl dimer dilinoleate, diisostearoyl trimethylolpropane siloxy silicate, diisostearyl adipate, diisostearyl dimer dilinoleate, diisostearyl malate, diisostearyl trimethylolpropane siloxy silicate, dilauroyl trimethylolpropane siloxy silicate, dilauryl trimethylolpropane siloxy silicate, dimethicone, dimethicone copolyol, dimethicone propyl PG-betaine, dimethiconol, dimethyl isosorbide, dioctyl maleate, dioctylodedecyl dimer dilonoleate, ethylhexyl benzoate, ethylhexyl cocoate, ethylhexyl dimethyl PABA, ethylhexyl ethylhexanoate, ethylhexyl hydroxystearate, ethylhexyl hydroxystearate benzoate, ethylhexyl isononanoate, ethylhexyl isopalmitate, ethylhexyl isostearate, ethylhexyl laurate, ethylhexyl methoxycinnamate, ethylhexyl myristate, ethylhexyl neopentanoate, ethylhexyl oleate, ethylhexyl palmitate, ethylhexyl salicylate, ethylhexyl stearate, glyceryl caprate, glyceryl caprylate, glyceryl caprylate/caprate, glyceryl cocoate, glyceryl dilaurate, glyceryl dioleate, glyceryl hydroxystearate, glyceryl isostearate, glyceryl laurate, glyceryl oleate, glycol oleate, glycol ricinoleate, *helianthus annuus* (hybrid sunflower) seed oil, *helianthus annuus* (sunflower) seed oil, homosalate, isoamyl laurate, isoamyl p-methoxycinnamate, isocetyl alcohol, isocetyl behenate, isocetyl ethylhexanoate, isocetyl isostearate, isocetyl laurate, isocetyl linoleoyl stearate, isocetyl myristate, isocetyl palmitate, isocetyl salicylate, isocetyl stearate, isocetyl stearoyl stearate, isohexadecane, isononyl isononanoate, isopropyl C12-15-pareth-9 carboxylate, isopropyl isostearate, isopropyl lanolate, isopropyl laurate, isopropyl linoleate, isopropyl methoxycinnamate, isopropyl myristate, isopropyl oleate, isopropyl palmitate, isopropyl PPG-2-isodeceth-7 carboxylate, isopropyl ricinoleate, isopropyl stearate, isostearic acid, isostearyl alcohol, isostearyl ethylhexanoate, isostearyl isononanoate, isostearyl isostearate, isostearyl lactate, isostearyl myristate, isostearyl neopentanoate, isostearyl palmitate, isostearyl stearoyl stearate, jojoba oil, lanolin (lanolin oil), maleated soybean oil, myristyl isostearate, myristyl lactate, myristyl myristate, myristyl neopentanoate, myristyl stearate, octocrylene, octyldecanol, octyldodecanol, *oenothera biennis* (evening primrose oil), paraffinum liquidum (mineral oil), PCA dimethicone, pentaerythrityl tetraisononanoate, pentaerythrityl tetraisostearate, perfluoropolymethylisopropyl ether, *persea gratissima* (avocado oil), phenyl trimethicone, PPG-15 stearyl ether, propylene glycol ceteth-3 acetate, propylene glycol dicaprylete, propylene glycol dicaprylate/dicaprate, propylene glycol dipelargonate, propylene glycol distearate, propylene glycol isoceteth-3 acetate, propylene glycol isostearate, propylene glycol laurate, proylene glycol ricinoleate, propylene glycol stearate, *prunus dulcis* (sweet almond oil), squalane, squalene, tricaprylin, tricaprylyl citrate, tridecyl ethylhexanoate, tridecyl neopentanoate, tridecyl stearoyl stearate, triethylhexanoin, triethylhexyl citrate, trihydroxystearin, triisocetyl Citrate, triisostearin, triisostearyl citrate, trimethylolpropane triisostearate, trimethylsiloxysilicate, *triticum vulgare* (wheat germ oil), *vitis vinifera* (grape) seed oil, and mixtures thereof.

A preferred organic medium continuous phase for use in the dispersion of the present invention comprises as major component or substrate a glyceride oil, more preferably a triglyceride oil. More particularly, the glyceride oil is made using generally medium chain fatty acid species, especially fatty acids having a chain length of 16 carbon atoms or less, although up to about 10% by weight of the starting material may have a chain length greater than $C_{16}$. Most preferably, the fatty acids used to make the glyceride oils range from about $C_6$ to about $C_{14}$. The acid species can be saturated or unsaturated, linear or branched, substituted or unsubstituted. Preferred materials include medium chain (mostly based on $C_{14}$ acids or less) triglycerides, particularly caprylic/capric triglyceride.

The organic medium continuous phase for use in the dispersion of the present invention preferably comprises, consists essentially of, or consists of at least one polar material, suitably having an interfacial tension compared to water in the range from 5 to 30, preferably 12 to 25, more preferably 15 to 23, particularly 18 to 22, and especially 19 to 21 $mNm^{-1}$ (measured by the Du Nouy Ring method at 25° C.). Where mixtures of polar materials are used, it is preferred that the mean interfacial tension value falls within the above preferred mentioned ranges.

Suitable polar materials comprise, or are selected from the group consisting of, C12-15 alkyl benzoate, caprylic/capric triglyceride, cetearyl isononanoate, ethylhexyl isostearate, ethylhexyl palmitate, isononyl isononanoate, isopropyl isostearate, isopropyl myristate, isostearyl isostearate, isostearyl neopentanoate, octyldodecanol, pentaerythrityl tetraisostearate, PPG-15 stearyl ether, triethylhexyl triglyceride, dicaprylyl carbonate, ethylhexyl stearate, *helianthus annus* (sunflower) seed oil, isopropyl palmitate, octyldodecyl neopentanoate, and mixtures thereof. Preferred polar materials are triethylhexyl triglyceride, C12-15 alkyl benzoate, caprylic/capric triglyceride, isononyl isononanoate, isostearyl neopentanoate, and octyldodecyl neopentanoate, and particularly preferred is caprylic/capric triglyceride e.g. CRODAMOL GTCC (caprylic/capric triglyceride, ex Croda).

An alternative preferred organic medium continuous phase for use in the dispersion of the present invention comprises, consists essentially of, or consists of at least one mineral oil, particularly light mineral oil.

The concentration of organic medium or substrate in a dispersion according to the present invention is preferably in the range from 20 to 80%, more preferably 25 to 65%, particularly 30 to 55%, and especially 35 to 50% by weight based on the total weight of the dispersion.

The non-ionic surfactant used in the invention may be an alkoxylate surfactant and/or surfactant derived from natural materials such as fatty acid esters, ethers, hemi-acetals or acetals of polyhydroxylic compounds or a fatty acid amide which is N-substituted with the residue of a polyhydroxylic compound. The hydrophobe, usually a hydrocarbyl group, of the non-ionic surfactant is typically a chain, commonly an alkyl chain, preferably containing from 8 to 24, more preferably 12 to 22, and particularly 14 to 20 carbon atoms.

The term alkoxylate surfactant is used to refer to surfactants in which the hydrophobe is connected through the residue of a linking group having a reactive hydrogen atom to an oligomeric or polymeric chain of alkylene oxide residues (the hydrophile). The linking group can be an oxygen atom (hydroxyl group residue); a carboxyl group (fatty acid or ester residue); an amino group (amine group residue); or a carboxyamido (carboxylic amide residue). The alkylene oxide residues are typically residues of ethylene oxide ($C_2H_4O$) or propylene oxide ($C_3H_6O$) or combinations of ethylene and propylene oxide residues. When combinations are used, the proportion of ethylene oxide residues will usually be at least about 50 mole % and more usually at least 75 mole %, the remainder being propylene oxide residues. In a preferred embodiment, substantially all of the residues are ethylene oxide residues. The number of alkylene residues in the surfactant molecule is preferably from 2 to about 200. Alkyl phenyl ethoxylates could be used, but these are generally not now desired in personal care applications.

Examples of suitable alkoxylate surfactants include alcohol alkoxylates, of the formula (Ia): $R^1$—O-(AO)$_n$—H; a fatty acid alkoxylate of the formula (Ib): $R^1$—COO-(AO)$_n$—$R^2$ (plus co-products); a fatty amine alkoxylate of the formula (Ic): $R^1$—$NR^3$-(AO)$_n$—H; or a fatty amide alkoxylate of the formula (Id); $R^1$—$NR^3$-(AO)$_n$—H, where each $R^1$ is independently a $C_8$ to $C_{24}$, particularly $C_{12}$ to $_{22}$, hydrocarbyl, particularly alkyl group; $R^2$ is a hydrogen atom or a $C_1$ to $C_6$ alkyl group; and each $R^3$ is independently a $C_1$ to $C_6$ alkyl group or a group (AO)$_n$—H; each AO is independently an ethylene oxide or propylene oxide group; and the total of the indices n in the molecule is from 2 to 200.

In a preferred embodiment, non-ionic surfactants that are not derivatives of alkylene oxides are used, i.e. the non-ionic surfactant(s) is/are derived entirely from biological, particularly vegetable, source materials. The non-ionic surfactant is preferably a fatty acid ester, ether, hemi-acetal or acetal of a polyhydroxylic compound, or a fatty acid amide which is N-substituted with the residue of a polyhydroxylic compound, especially a saccharide fatty acid ester.

Particularly useful esters of polyhydroxylic compounds include saccharide esters particularly mono-esters of fatty acids and a sugar, especially sucrose, fructose and/or glucose. Commercially available sugar esters are usually mixtures containing mono-ester, higher esters and sometimes free starting material (sugar). In this invention it is desirable to use sugar esters having a relatively high proportion of mono-ester. Typically the sugar ester used will have a content of mono-ester of at least 50% more usually at least 60% and desirably at least 65%. The proportion may be higher e.g. 70%, 80% or even higher, although products with very high proportions of mono-ester are significantly more expensive. Sugar esters are relatively hydrophilic surfactants and less hydrophilic variants can be used in which hydroxyl groups (usually only one) on the saccharide residue are etherified (or acetalated) typically with a $C_1$ to $C_4$ alkyl group e.g. a methyl group. Desirable sugar esters may be of the formula (IIa): $R^1$—COO-(G)$_a$, where $R^1$ is as defined above for alkoxylate surfactants; each G is independently a saccharide residue, particularly a glucose, mannose or fructose residue and a is from 1 to about 6, particularly about 2, especially the residue (G)$_a$ is the residue of sucrose or glucose.

Other esters of polyhydroxylic compounds include esters of fatty acids, preferably fatty acids having from 8 to 24, more preferably 12 to 22, and particularly 16 to 20 carbon atoms, and polyols particularly glycerol, or a polyglycerol, or an anhydro-saccharide such as sorbitan. Generally, these materials are desirably also mainly used as the mono-ester. Examples include glycerol mono-laurate, triglycerol mono-stearate and among relatively more hydrophobic surfactants glycerol mono-stearate and sorbitan mono-oleate, -stearate, -isostearate or -laurate. Suitable such esters may be of the formula (IIb): $R^1$—COO—$R^4$, where $R^1$ is as defined above for alkoxylate emulsifiers; and $R^4$ is a polyhydroxyl hydrocarbyl group, particularly an alkyl group or alkyl ether group containing from 3 to 10 carbon atoms and 2 to 6 hydroxyl groups.

Other ester surfactants include fatty acid esters of hydroxycarboxylic acids, in particular the products of trans esterification between fatty glycerides, especially mono- and di-glycerides, and polyhydroxy-carboxylic acids. These products are usually described as esters, but are typically mixtures of the starting materials and the trans-esterification products, particularly where the fatty acid residues are esterified to hydroxyl groups on the hydroxycarboxylic acids. In these products, the fatty acid preferably has from 8 to 24, more preferably 12 to 22, particularly 16 to 20 carbon atoms, and the hydroxycarboxylic acid is preferably citric acid.

Another type of non-ionic surfactant derived from sugars are saccharide hydrocarbyl ethers, hemi-acetals or acetals, commonly known as hydrocarbyl, particularly alkyl, polysaccharides (more properly oligo saccharides), and in particular materials of the formula (IIc): $R^1$—O-(G)$_a$, where $R^1$ is as defined above for alkoxylate surfactants; each G is independently a saccharide residue, particularly a glucose residue and a is from 1 to about 5, particularly from about 1.3 to about 2.5.

A further non-ionic surfactant type is of N-substituted fatty acid amides in which the N-substituent is the residue of a polyhydroxylic compound, which is commonly a saccharide residue such as a glucosyl group. This type of surfactant includes materials of the formula (IId): $R^1$—CO—$NR^5R^6$, where $R^1$ is as defined above for alkoxylate surfactants; $R^5$ is a hydrogen atom, a $C_1$ to $C_6$ alkyl group or a group of the formula $R^6$; and $R^6$ is a polyhydroxyl hydrocarbyl group, particularly a group containing from 3 to 10 carbon atoms and 2 to 6 hydroxyl groups, and is typically a glucosyl residue.

In a preferred embodiment, the non-ionic surfactant is relatively hydrophobic, i.e. preferably has a Hydrophile Lipophile Balance (HLB) of not more than 10, more preferably not more than 9, and particularly not more than 8. Such non-ionic surfactants are preferably selected from the group consisting of alkoxylate surfactants with an average of from 2 to about 10 alkylene oxide, particularly ethylene oxide residues; glycerol esters where the fatty acid has 14 to 24 carbon atoms such as glycerol mono-stearate, -oleate, or -laurate; and anhydrosaccharide fatty esters such as sorbitan mono-stearate, -isostearate, -cocoate, -oleate, or -laurate. In a preferred embodiment, the non-ionic surfactant is selected from the group consisting of sorbitan oleates, sorbitan cocoates, sorbitan stearates, sorbitan isostearates, alkoxylated fatty acids, alkoxylated fatty alcohols, glycerol mono-oleates, glycerol isostearates, polyglycerol oleates, polyglycerol ricinoleates and polyglycerol isostearates, and mixtures thereof. Polyglycerol ricinoleate is one preferred non-ionic surfactant e.g., Crester™ PR (ex Croda). In a particularly preferred embodiment, the non-ionic surfactant comprises an ester of an anhydro-saccharide, more preferably a sorbitan ester such as oleate, -cocoate, stearate, isostearate or laurate. Sorbitan isostearate e.g. Crill™ 6 (ex Croda), and sorbitan cocoate e.g. Crill™ 1 (ex Croda), are especially preferred non-ionic surfactants.

It may be useful to use a combination of different types of surfactant, and in particular to combine hydrophilic non-ionic surfactants, i.e. having a high HLB, e.g. preferably more than 10, more preferably more than 12, and hydrophobic non-ionic surfactants, i.e. preferably having a low HLB, e.g. preferably less than 10, more preferably less than 8, in making the dispersions of the invention. Relatively hydrophilic non-ionic surfactants include alkoxylate emulsifiers with an average of from about 10 to about 100 alkylene oxide, particularly ethylene oxide residues; and non-alkoxylate non-ionic surfactants including sugar mono-esters and polyglycerol mono-esters, hydrocarbyl, especially alkyl, polysaccharides; fatty acid glycerol esters where the fatty acid has 8 to 12 carbon atoms such as glycerol mono-laurate and fatty acid N-sugar amides such as glucamides. Relatively hydrophobic non-ionic surfactants include alkoxylate surfactants with an average of from 2 to 10 alkylene oxide, particularly ethylene oxide residues; glycerol esters where the fatty acid has 14 to 24 carbon atoms such as glycerol mono-stearate, -isostearate, -oleate, -cocoate, or -laurate; and anhydrosaccharide fatty esters such as sorbitan mono-stearate, -isostearate, -oleate, -cocoate, or -laurate.

It is generally technically possible to freely combine non-ionic surfactants of the alkoxylate and non-alkoxylate types described above. Such combinations may be attractive where the dispersion includes a hydrophilic alkoxylate surfactant, e.g. using a low HLB non-alkoxylate surfactant in combination. However, hydrophilic non-alkoxylate surfactants, especially sugar mono-ester surfactants, are more expensive than typical alkoxylate surfactants and will usually be used only when it is desired to have a surfactant system which includes no derivatives of alkylene oxides.

The concentration of non-ionic surfactant in a dispersion according to the present invention is suitably in the range from 0 to 40%, preferably 2 to 25%, more preferably 5 to 15%, particularly 6 to 12%, and especially 7 to 11% by weight based on the total weight of the dispersion.

The emollient ester used in the dispersion of the present invention is preferably an alkoxylated ester, more preferably a propoxylated ester. The emollient ester is preferably derived from alkoxylated alcohols and carboxylic acids. The emollient ester is preferably miscible in the organic medium continuous phase, and more preferably immiscible in water.

The emollient ester is preferably selected from the group consisting of the reaction products of a monoprotic or monocarboxylic acid, di- or tri-carboxylic acids having 2 to 12 carbon atoms, more preferably having 4 to 6 carbon atoms, and mixtures thereof reacted with alkoxylated fatty alcohols of between 6 and 22 carbon atoms and mixtures thereof, the alkoxy group being on average between 2 to 3 carbon atoms, inclusively, in length and being present in about 2 to about 50 units on average in each molecule.

It will be appreciated that the carboxylic acids, fatty alcohols and alkoxy groups used in reactions to produce the preferred alkoxylated emollient esters used in the present invention often contain a variety of similar compounds of various carbon chain lengths, especially when derived from natural resources and references to specific acids and alcohols refer to the primary or major components of the materials used.

More preferably, the emollient ester is selected from the group consisting of the reaction products of di- or tri-carboxylic acids having 4 to 6 carbon atoms and mixtures thereof reacted with alkoxylated fatty alcohols of between 10 and 18 carbon atoms, more preferably between 12 and 16 carbon atoms, and mixtures thereof, the alkoxy group having an average of between 2 and 3 carbon atoms, inclusively, in length and being present in about 2 to about 10 units on average in each molecule, more preferably about 2 to about 5 units on average in each molecule.

Particularly preferred carboxylic acids include the dicarboxylic acids maleic, succinic and adipic acids and the tricarboxylic acid citric acid.

The fatty alcohols may be straight or branched, substituted or unsubstituted, saturated, unsaturated or polyunsaturated. They preferably have between 6 and 22 carbons in length, more preferably between 10 and 18 carbons in length. It is not necessary that each fatty alcohol group be the same, and thus the emollient esters may be asymmetrically substituted.

The alkoxy groups useful in the preferred alkoxylated emollient esters used in the present invention are generally short chain alkoxy groups of between 2 and 3 carbons, i.e. ethoxy and propoxy groups. Most preferred of the propoxy groups are the branched propoxy, wherein a methyl group is attached to the first or second carbon of the chain. Mixtures of propoxy groups may be present. Alkoxy substituents can be homogeneous (for example, all ethoxy) or may be a mixture of ethoxy and propoxy and/or a mixture of different forms of propoxy groups. Where different forms of propoxy and/or propoxy and ethoxy groups are used, the order can be random or in blocks. Each group may be considered a separate unit and the average number of alkoxy units in each molecule will generally range from between 1 and 50, preferably between 1 and 30, more preferably between 2 and 15.

Especially preferred emollient esters are di-PPG-3-myristyl ether adipate and tri-PPG-3 myristyl ether citrate, particularly tri-PPG-3 myristyl ether citrate.

The emollient ester preferably has a Hansen and Beerbower solubility parameter in the range from 15 to 25, more preferably 17 to 22, particularly 18.5 to 21, and especially 19.5 to 20.

The Required HLB value of the emollient ester is preferably in the range from 3 to 10, more preferably 4 to 8, particularly 4.5 to 6, and especially 5 to 5.5.

The concentration of emollient ester in a dispersion according to the present invention is suitably in the range from 0 to 40%, preferably 2 to 30%, more preferably 5 to 25%, particularly 8 to 18%, and especially 11 to 14% by weight based on the total weight of the dispersion.

In a particularly preferred embodiment of the invention the dispersion comprises both an emollient ester and a non-ionic surfactant as described herein.

In one embodiment of the present invention, the dispersion comprises, consists essentially of, or consists of a carboxylic acid polymer dispersed in an organic medium liquid phase of (i) a fatty alcohol, glycol, glyceride oil, vegetable oil, ester oil, fatty alcohol alkoxylate, alkyl carbonate, mineral oil and silicone oil, and mixtures thereof, (ii) a non-ionic surfactant, and (iii) an emollient ester. Component (i) preferably has an interfacial tension compared to water of from 12 to 25, more preferably 15 to 23 $mNm^{-1}$; and/or component (ii) preferably has a HLB value of not more than 10, more preferably not more than 9; and/or component (iii) preferably has Hansen and Beerbower solubility parameter of 17 to 22, more preferably 18.5 to 21. Particularly preferred components are (i) a glyceride oil, especially caprylic/capric triglyceride, (ii) a sorbitan ester, especially sorbitan isostearate and/or sorbitan cocoate, and/or (iii) di-PPG-3-myristyl ether adipate and/or tri-PPG-3 myristyl ether citrate, especially tri-PPG-3 myristyl ether citrate.

In one preferred embodiment of the invention, the dispersion is obtained by forming a liquid phase by mixing together the organic medium comprising emollient ester and/or non-ionic surfactant, and then dispersing the carboxylic acid polymer, in particulate form, in the liquid phase. Preferably low shear mixing is used, such as with a paddle mixer. In a further preferred embodiment, the mixing occurs without heating, i.e. at low or ambient temperature.

It has been found that, in the dispersions of the present invention, the carboxylic acid polymer component is stably dispersed. As a consequence, the dispersions are particularly effective, when used to make oil-in-water or water-in-oil emulsions, especially end-use emulsions or formulated products which form a further embodiment of the present invention.

The concentration of dispersion used to form an end-use emulsion or formulated product is suitably in the range from 0.05 to 5%, preferably 0.1 to 2%, more preferably 0.2 to 1%, particularly 0.25 to 0.5%, and especially 0.3 to 0.4% by weight based on the weight of the emulsion.

Without being bound to any particular theory, it is thought that the liquid phase of the dispersion according to the invention is particularly effective in decreasing agglomeration and/or untangling of the polymer chains of the carboxylic acid polymers, thus enabling them to be dispersed to a greater extent than is normally experienced when using such carboxylic acid polymers. The more effective dispersion of the polymer chains also enables them to function more effectively when formulating emulsions using the dispersions of the present invention. The higher availability of the polymer chains may be inferred by the fact that dispersions according to the invention require a greater amount of pH adjustor, for example triethanolamine, to be added when being neutralised to achieve a pH of 6 to 7 (typically required to maximise thickening or stabilizing properties of the carboxylic acid polymers) as compared to a typical known emulsion containing the carboxylic acid polymer. The use of a greater amount of pH adjustor indicates a requirement to neutralise a greater amount of residual acid and hydroxy groups as compared to those requiring neutralisation in the known emulsions. This suggests that, in the dispersions according to the present invention, such residual groups are significantly more available to be neutralized.

In one embodiment, the dispersion according to the present invention is used in combination with a water miscible (or soluble) emollient ester to form an end-use emulsion.

The water miscible emollient ester preferably has a Hansen and Beerbower solubility parameter in the range from 20 to 30, more preferably 21 to 27, particularly 22 to 25, and especially 23 to 24.

In addition, the water miscible emollient ester preferably has a HLB value in the range from 8 to 18, more preferably 9 to 14, particularly 10 to 12, and especially 10.5 to 11.

The water miscible emollient ester is preferably an alkoxylated ester, and more preferably an ethoxylated ester. Alkoxylated glycerides are preferred, particularly glycerides derived from $C_6$ to $C_{20}$, preferably $C_8$ to $C_{18}$ fatty carboxylic acids, typically derived from renewable resources such as coconut oil and palm kernel oil. The alkoxy groups of such glycerides are generally short chain alkoxy groups of between 2 and 3 carbons, i.e. ethoxy and propoxy groups. Mixtures of propoxy groups may be present. Alkoxy substituents can be homogeneous (for example and preferably, all ethoxy) or may be a mixture of ethoxy and propoxy and/or a mixture of different forms of propoxy groups. Where different forms of propoxy and/or propoxy and ethoxy groups are used, the order can be random or in blocks. Most preferred of the ethoxy groups. Each group may be considered a separate unit and the average number of alkoxy units in each molecule will preferably be in the range from 1 to 100, more preferably 1 to 50, and particularly between 2 to 15.

Particularly preferred alkoxylated glycerides are selected from the group consisting of ethoxy cocoate glycerides, ethoxy capric/caprylic glycerides and ethoxy palm kernel glycerides, especially ethoxy cocoate glycerides, e.g. PEG-7 glyceryl cocoate (Glycerox™ HE (ex Croda)).

The dispersion described herein and water miscible emollient ester may be added as separate ingredients in the formation of an emulsion. In which case, (i) the concentration of the dispersion used is preferably in the range from 0.05 to 2%, more preferably 0.1 to 1%, particularly 0.2 to 0.5%, and especially 0.3 to 0.4% by weight based on the weight of the emulsion; and (ii) the concentration of water miscible emollient used is preferably in the range from 0.1 to 5%, more preferably 0.2 to 3%, particularly 0.3 to 2%, and especially 0.5 to 1% by weight based on the weight of the emulsion.

However in an alternative embodiment, the dispersion and water miscible emollient ester and/or a non-ionic surfactant having a HLB value of greater than or equal to 8, are pre-mixed together, preferably with water to form a composition, preferably clear or translucent, having a gel like consistency (gel or a thick liquid (hereinafter referred to as a gel)). The gel compositions are preferably clear, soft gels at room temperature that are readily water soluble and exhibit good thermal stability. The gel composition forms a further embodiment of the present invention.

The gel is also particularly effective, when used to make oil-in-water or water-in-oil emulsions. A combination of both the dispersion and gel may also be used to form end-use emulsions.

The gel composition preferably comprises, consists essentially of, or consists of (i) optionally water, (ii) an organic medium, (iii) a water miscible emollient ester and/or a non-ionic surfactant having a HLB value of greater than or equal to 8, preferably up to 18, (iv) an emollient ester miscible in the organic medium and/or a non-ionic surfactant, and (v) a carboxylic acid polymer.

The non-ionic surfactant having a HLB value of greater than or equal to 8 may be any of the suitable herein described surfactants.

The concentration of dispersion defined herein used to form the gel is suitably in the range from 0.5 to 40%, preferably 2 to 35%, more preferably 3 to 30%, particularly 4 to 25%, and especially 5 to 20% by weight based on the weight of the composition.

The concentration of water miscible emollient ester and/or a non-ionic surfactant having a HLB value of greater than or equal to 8, in the gel is suitably in the range from 30 to 90%, preferably 40 to 85%, more preferably 50 to 80%, particularly 60 to 72%, and especially 64 to 68% by weight based on the weight of the composition.

The concentration of water in the gel is suitably in the range from 0 to 60%, preferably 1 to 50%, more preferably 3 to 40%, particularly 4 to 35%, and especially 5 to 30% by weight based on the weight of the composition.

The concentration of carboxylic acid polymer in the gel is suitably in the range from 0.3 to 15%, preferably 0.6 to 10%, more preferably 0.9 to 8%, particularly 1.2 to 6%, and especially 1.5 to 5% by weight based on the weight of the composition.

The gel composition of the invention may contain other ingredients if desired, for example additional non-ionic surfactants, as hereinbefore described.

One preferred gel composition according to the invention comprises, consists essentially of, or consists of (i) 20 to 35%, more preferably 25 to 30% by weight of water, (ii) 1 to 10%, more preferably 3 to 7% by weight of a dispersion as defined herein, and (iii) 60 to 75%, more preferably 65 to 70% by weight a water miscible emollient ester having a Hansen and Beerbower solubility parameter of 21 to 27, more preferably 22 to 25.

An alternative preferred gel composition according to the invention comprises, consists essentially of, or consists of (i) 2 to 15%, more preferably 5 to 10% by weight of water, (ii) 10 to 25%, more preferably 15 to 20% by weight of a dispersion as defined herein, (iii) 60 to 75%, more preferably 65 to 70% by weight a water miscible emollient ester having a Hansen and Beerbower solubility parameter of 21 to 27, more preferably 22 to 25, and (iv) 5 to 13%, more preferably 8 to 10% by weight of a non-ionic surfactant, preferably having a HLB value of less than 8.

The concentration of the gel used to form an end-use emulsion is preferably in the range from 0.5 to 20%, more preferably 1 to 10%, particularly 2 to 6%, and especially 3 to 5% by weight based on the weight of the emulsion.

In a further embodiment of the invention, the dispersion and/or gel composition, preferably dispersion, defined herein can be used to produce an emulsification system or pre-emulsion (or concentrated emulsion) which can also be used to produce end-use emulsions or formulated products. The emulsification system is preferably in the form of an oil-in-water emulsion. The emulsification system can be considered to be a complete formulated system enabling stable oil-in-water or water-in-oil emulsions to be formed by the simple addition of water and/or oil(s) together with any required active ingredients, i.e. without the requirement of having to add further non-ionic surfactants or emulsifiers. This gives the end-use formulator great flexibility in being able to form a wide range of emulsions from a single emulsification system, particularly at low or ambient temperature, and especially by low shear mixing.

The concentration of dispersion and/or gel composition, preferably dispersion, defined herein used to form the emulsification system according to the invention is suitably in the range from 0.5 to 20%, preferably 1 to 10%, more preferably 2 to 5%, particularly 2.5 to 3.5%, and especially 2.7 to 3.3% by weight based on the weight of the composition.

The emulsification system preferably comprises, consists essentially of, or consists of (i) water, (ii) an oil, (iii) a non-ionic surfactant, (iv) optionally a water miscible emollient ester, and (v) a carboxylic acid polymer.

The concentration of water in the emulsification system is suitably in the range from 10 to 60%, preferably 15 to 50%, more preferably 20 to 40%, particularly 25 to 35%, and especially 28 to 32% by weight based on the weight of the system.

The oil component or oil phase of the emulsification system may comprise one or more of the organic media described herein for forming the dispersion, and suitably comprises the same preferred materials, i.e. particularly a glyceride oil.

The concentration of oil in the emulsification system is suitably in the range from 15 to 70%, preferably 20 to 60%, more preferably 25 to 50%, particularly 30 to 45%, and especially 35 to 40% by weight based on the weight of the system.

The non-ionic surfactant component of the emulsification system may comprise one or more of the non-ionic surfactants described herein for forming the dispersion. The non-ionic surfactant component functions as an emulsifier, particularly as an oil-in-water emulsifier. Preferably a combination of high and low HLB non-ionic surfactants as described herein is employed.

The concentration of non-ionic surfactant in the emulsification system is suitably in the range from 3 to 30%, preferably 8 to 28%, more preferably 12 to 26%, particularly 16 to 24%, and especially 20 to 22% by weight based on the weight of the system.

The non-ionic surfactant component in the emulsification system preferably comprises, consists essentially of, or consists of (i) in the range from 1 to 6%, more preferably 2 to 4%, particularly 2.5 to 3.5%, and especially 2.8 to 3.2% by weight based on the weight of the system of a non-ionic surfactant having a HLB value of greater than 10, preferably greater than 12, (ii) in the range from 2 to 12%, more preferably 4 to 8%, particularly 5 to 7%, and especially 5.5 to 6.5% by weight based on the weight of the system of a non-ionic surfactant having a HLB value of greater than 2.5 and less than 10, preferably greater than 3 and less than 8, and (iii) in the range from 2 to 18%, more preferably 6 to 16%, particularly 10 to 14%, and especially 11 to 13% by weight based on the weight of the system of a non-ionic surfactant having a HLB value of less than 2.5, preferably about 2.

The water miscible emollient ester component of the emulsification system may comprise one or more of the water miscible emollient esters described herein for use in combination with the dispersion according to the invention, and suitably comprises the same preferred materials, i.e. particularly an alkoxylated emollient ester.

The concentration of water miscible emollient ester in the emulsification system is suitably in the range from 0 to 25%, preferably 4 to 20%, more preferably 7 to 15%, particularly 9 to 11%, and especially 9.5 to 10.5% by weight based on the weight of the system.

The concentration of carboxylic acid polymer in the emulsification system is suitably in the range from 0.1 to 5%, preferably 0.4 to 2%, more preferably 0.6 to 1.3%, particularly 0.7 to 1.1%, and especially 0.8 to 1.0% by weight based on the weight of the composition.

The emulsification system of the invention may contain other ingredients if desired, for example additional non-ionic surfactants, as hereinbefore described.

One preferred emulsification system according to the invention comprises, consists essentially of, or consists of (i) 20 to 40%, more preferably 25 to 35% by weight of water, (ii) 25 to 50%, more preferably 30 to 45% by weight of oil, (iii) 8 to 28%, more preferably 12 to 26% by weight of non-ionic surfactant, (iv) optionally 4 to 20%, more preferably 7 to 15% by weight a water miscible emollient ester having a Hansen and Beerbower solubility parameter of 21 to 27, more preferably 22 to 25, and (v) 2 to 5%, more preferably 2.5 to 3.5% by weight of a dispersion as defined herein.

The concentration of the emulsification system used to form an end-use emulsion or formulated product is preferably in the range from 5 to 60%, more preferably 10 to 45%, particularly 15 to 35%, and especially 20 to 30% by weight based on the weight of the emulsion.

As described herein the dispersion, gel composition and/or emulsification system according to the present invention may be used to form end-use emulsions or formulated products, which forms a further embodiment of the invention. It is normally necessary to adjust the pH, e.g. by addition of a suitable base such as triethanolamine, after emulsification in order to neutralise the carboxylic acid polymer to achieve stabilisation and the desired viscosity.

The concentration of the oil phase in the end-use emulsions according to the present invention may vary widely. Generally the oil phase concentration will be at least 15%, and more usually at least about 25% by weight based on the weight of the emulsion. A particularly advantageous feature of the invention is that the dispersions and/or gels and/or emulsification systems described herein can be used to produce stable, suitably oil-in-water, emulsions at a high oil concentration preferably greater than 50%, more preferably greater than 60%, particularly greater than 70%, and especially greater than 80% and up to 90% by weight based on the weight of the emulsion. Such high oil concentrations can even be achieved for difficult to emulsify oils such as silicone oils.

The oil phase of the emulsion will comprise (from the addition of the dispersion and/or gel and/or emulsification system) one or more of the organic media described above for forming the dispersion, but one or more additional organic media may, and normally will be, added as a separate component. The oil phase will typically mainly be an oil of the type widely used in personal care or cosmetic products. The oil is preferably liquid at ambient temperature. Alternatively it can be solid at ambient temperature, in which case in bulk it will usually be a waxy solid, provided it is liquid at an elevated temperature at which it can be included in and emulsified in the composition.

Suitable normally liquid oils include non-polar oils, for example mineral or paraffin, especially isoparaffin, oils, such as that sold by Croda as ARLAMOL HD; or medium polarity oils, for example vegetable glyceride oils such as jojoba oil, animal glyceride oils, such as that sold by Croda as ESTOL™ 3600 (triethylhexanoin), caprylic/capric triglycerides, such as that sold by Croda as CRODAMOL GTCC (caprylic/capric triglyceride), synthetic oils, for example synthetic ester oils, such as isopropyl isostearate and propylene glycol isostearates sold by Croda as PRISORINE 2021 and PRISORINE 2034 respectively, C12-C15 alkyl benzoates or ether oils, particularly of two fatty e.g. $C_8$ to $C_{18}$ alkyl residues, such as that sold by Henkel as EUTANOL G (octyl dodecanol), or silicone oils, such as dimethicone oil such as those sold by Dow Corning as DC2, cyclomethicone oil as sold by Dow Corning as DC245, or silicones having polyoxyalkylene side chains to improve their hydrophilicity; or highly polar oils including alkoxylate emollients for example fatty alcohol propoxylates such as that sold by Croda as ARLAMOL E (stearyl alcohol 15-propoxylate) or alkyl carbonates such as CETIOL CC (INCI: Dicapryl Carbonate) ex-Cognis.

The emulsion may also comprise (from the addition of the dispersion and/or gel and/or emulsification system) one or more of the non-ionic surfactants described above for forming the dispersion, but one or more additional non-ionic surfactants may, and normally will be, added as a separate component of the emulsion when the dispersion and/or gel is employed.

One advantage of the dispersions, gels and emulsification systems according to the present invention is that they can be used to form emulsions at low temperatures, for example below 50° C., more preferably below 40° C., particularly below 30° C., and especially even at ambient temperature (23° C.). For cold processing, it is preferred that the components of the oil phase are liquid at ambient temperature, or that any solid or waxy components are soluble or dispersible in the liquid components. A further advantage is that emulsions can be formed at low shear, for example using a paddle mixer, preferable in a single pot.

Other advantages of using dispersions, gels and emulsification systems according to the present invention to produce emulsions can include one or more of the following; reduced mixing and wet out times, reduced grainy texture, improved viscosity and stability, more robust gel formation, improved skin feel including less tackiness, and/or reduction in "fish eyes".

The emulsions according to the present invention are suitably stable, measured as described herein, preferably for greater than one month, more preferably greater than two months, particularly greater than three months, and especially greater than four months at 5° C., and/or at ambient temperature (23° C.), and/or at 43° C. The stability at even higher temperatures can also be important, and therefore the dispersions according to the invention are stable, measured as described herein, suitably for greater than one week, preferably greater than two weeks, more preferably greater than 3 weeks, particularly greater than one month, and especially greater than two months at 50° C.

Dispersions, gels and emulsification systems according to the present invention can be used in any application where polycarboxylic acid polymers, such as CARBOMER or Acrylates\C10-30 Alkyl Acrylate Crosspolymer, in particulate powder form have previously been used. The dispersions, gels and emulsification systems are particularly useful in forming emulsions such as lotions, creams and gels for personal care applications; silicone emulsions, mineral oil emulsions, wax emulsions for use in household and industrial e.g. in explosives, applications, for example in car polishes, furniture polishes, and tyre black. The dispersions, gels and emulsification systems can be used as thickeners, suspending aids, stabilizers for emulsions, and emulsion formers (can be used as a primary or secondary emulsifier). The dispersions and gels may also be used to make completely water- or solvent-free formulations containing silicones and waxes.

The dispersions, gels and emulsification systems are particularly suitable to be included in emulsion compositions to make personal care or cosmetic formulations. The emulsions may be incorporated into both milk and cream personal care products. Such emulsions may include many other components, which may be oil soluble, water soluble or non-soluble. Examples of such materials include:

(i) preservatives such as those based on parabens (alkyl esters of 4-hydroxybenzoic acid), phenoxyethanol, substituted ureas and hydantion derivatives e.g. those sold commercially under the trade names GERMABEN II Nipaguard BPX and Nipaguard DMDMH, when used usually in a concentration of from 0.5 to 2% by weight of the emulsion; (ii) perfumes, when used typically at a concentration of from 0.1 to 10% more usually up to about 5% and particularly up to about 2% by weight of the emulsion; (iii) humectants or solvents such as alcohols, polyols such as glycerol and polyethylene glycols, when used typically at a concentration of from 1 to 10% by weight of the emulsion; (iv) sunfilter or sunscreen materials including chemical sunscreens and physical sunscreens including those based on titanium dioxide or zinc oxide; when used typically at from 0.1% to 5% by weight of the emulsion; (v) alpha hydroxy acids such as glycolic, citric, lactic, malic, tartaric acids and their esters; (vi) self-tanning agents such as dihydroxyacetone; (vii) antimicrobial, particularly anti-acne components such as salicylic acid; (viii) vitamins and their precursors including:
- a) Vitamin A e.g. as retinyl palmitate and other tretinoin precursor molecules,
- b) Vitamin B e.g. as panthenol and its derivatives,
- c) Vitamin C e.g. as ascorbic acid and its derivatives,
- d) Vitamin E e.g. as tocopheryl acetate,
- e) Vitamin F e.g. as polyunsaturated fatty acid esters such as gamma-linolenic acid esters; (ix) skin care agents such as ceramides either as natural materials or functional mimics of natural ceramides; (x) phospholipids; (xi) vesicle-containing formulations; (xii) germanium-containing compounds, for example ARLAMOL GEO (ex Croda); botanical extracts with beneficial skin care properties; (xiii) skin whiteners such as dioic acid, for example ARLATONE Dioc DCA (ex Croda), hydroquinone, kojic acid, arbutin and similar materials; (xiv) skin repair compounds actives such as Allantoin and similar series; (xv) caffeine and similar compounds; (xvi) cooling additives such as menthol or camphor; (xvii) insect repellents such as N,N-diethyl-3-methyl-benzamide (DEET) and citrus or eucalyptus oils; (xviii) essential oils; and (xix) pigments, including microfine pigments, particularly oxides and silicates, e.g. iron oxide, particularly coated iron oxides, and/or titanium dioxide, and ceramic materials such as boron nitride, or other solid components, such as are used in make up and cosmetics, to give suspoemulsions, preferably used in an amount of from 1 to 5%, more preferably at least 5%, and particularly at least 10% by weight of the emulsion.

The personal care emulsions may be used in a wide range of compositions and end-use applications, such as moisturizers, sunscreens, after sun products, body butters, gel creams, high perfume containing products, perfume creams, baby care products, hair conditioners, skin toning and skin whitening products, water-free products, anti-perspirant and deodorant products, tanning products, cleansers, 2-in-1 foaming emulsions, multiple emulsions, preservative free products, emulsifier free products, mild formulations, scrub formulations e.g. containing solid beads, silicone in water formulations, pigment containing products, sprayable emulsions, colour cosmetics, conditioners, shower products, foaming emulsions, make-up remover, eye make-up remover, and wipes.

One preferred embodiment is as a sunscreen which contains one or more organic sunscreens and/or inorganic sunscreens such as metal oxides, but preferably comprises at least one particulate titanium dioxide and/or zinc oxide, particularly included in the composition in the form of an aqueous and/or organic dispersion available commercially from Croda under the trademarks TIOVEIL and SOLAVEIL CLAMS (both titanium dioxide) and SPECTRAVEIL (zinc oxide). In addition, organic sunscreens may be used together with the preferred metal oxide sunscreens, and include p-methoxy cinnamic acid esters, salicylic acid esters, p-amino benzoic acid esters, non-sulphonated benzophenone derivatives, derivatives of dibenzoyl methane and esters of 2-cyanoacrylic acid. Specific examples of useful organic sunscreens include benzophenone-1, benzophenone-2, benzophenone-3, benzophenone-6, benzophenone-8, benzophenone-12, isopropyl dibenzoyl methane, butyl methoxy dibenzoyl methane, ethyl dihydroxypropyl PABA, glyceryl PABA, octyl dimethyl PABA, octyl methoxycinnamate, homosalate, octyl salicylate, octyl triazone, octocrylene, etocrylene, menthyl anthranilate, 4-methylbenzylidene camphor, benzophenone 4, and phenyl benzimidazole sulphonic acid.

The invention is illustrated by the following non-limiting examples.

In this specification the following test method has been used to measure stability of the dispersion and emulsion:

Stability was assessed by observing the dispersion or emulsion after storage cold at 5° C., freezing/thawing at −18° C. (3 cycles), at ambient temperature (23° C.), or under elevated temperature storage at 43° C. and 50° C. The dispersion is stable if no visible settling of the polymer occurs (or if some settling out does occur, the particles can be easily re-dispersed by simple agitation). The emulsion is stable if no separation of the phases or creaming occurs.

EXAMPLES

Example 1

A dispersion was made by mixing, using a propeller stirrer at ambient temperature, the following ingredients:

10.8% by weight of CRILL 6 (sorbitan isostearate, ex Croda);

38.4% by weight of CRODAMOL GTCC (caprylic/capric triglyceride, ex Croda);

10.8% by weight of CROMOLLIENT TMC (tri-PPG-3 myristyl ether citrate, ex Croda; and 40% by weight of OPTASENSE G40 CARBOMER (polyacrylic acid, ex Croda).

The liquid phase ingredients were initially mixed together, and then the carboxylic acid polymer (Optasense™ G40) which is in powder form, was slowly introduced with continued stirring until a homogeneous dispersion was obtained.

Example 2

Amounts of the dispersion made in Example 1 between 0.1 to 2.5% by weight were stirred into water, and the aqueous dispersions were then neutralised to pH 6.5 by adding triethanolamine. The resultant aqueous compositions varied from watery, only slightly thickened compositions to very thick, hard gels as the amount of dispersion therein increased.

Example 3

The dispersion made in Example 1 was used (at amounts between 0.3 to 0.5% by weight) in combination with silicone oil, Glycerox™ HE (at amounts between 0.5 to 2.5% by weight) (PEG-7 glyceryl cocoate (ex Croda)), triethanolamine and water to make stable silicone emulsions in which the amount of silicone present varied from 10 to 90% by weight.

Example 4

A dispersion was made as described in Example 1 except that the following ingredients were used:

7% by weight of CRILL 1 (sorbitan cocoate, ex erode);
49% by weight of CRODAMOL GTCC (caprylic/capric triglyceride, ex Croda);
14% by weight of CROMOLLIENT TMC (tri-PPG-3 myristyl ether citrate, ex Croda); and
30% by weight of OPTASENSE G40 CARBOMER (polyacrylic acid, ex Croda).

A gel composition was made by mixing the 18.5% by weight of the dispersion with 9.3% by weight of Crill™ 4 (sorbitan oleate, ex Croda), 64.8% by weight of Glycerox™ HE (PEG-7 glyceryl cocoate (ex Croda)), and 7.4% by weight of water.

Example 5

A gel composition was made by mixing 5% by weight of the dispersion made in Example 4 with 68% by weight of Glycerox™ HE (PEG-7 glyceryl cocoate (ex Croda), and 27% by weight of water.

Example 6

End-use formulation silicone emulsions containing up to 90% by weight of silicone were made using the gel composition made in Example 4, and the dispersion made in Example 1. The emulsions were made using the ingredients shown in Table 1.

TABLE 1

| Ingredient | Sample 1 (% by weight) | Sample 2 (% by weight) | Sample 3 (% by weight) | Sample 4 (% by weight) |
|---|---|---|---|---|
| Silicone | 10 | 30 | 50 | 90 |
| Gel composition | 0.75 | 1.5 | 2.6 | 3.65 |
| Dispersion | 0.25 | 0.4 | 0.37 | — |
| Water | 89 | 68.1 | 47.03 | 6.35 |
| Triethanolamine | qs | qs | qs | qs |
| Total | 100 | 100 | 100 | 100 |

The silicone was premixed with the gel composition and the dispersion. This mixture was then slowly added to water with high speed stirring. The pH of the resultant formulation was adjusted to 6 to 7 using the triethanolamine.

In respect of Sample 1, the amounts of gel composition and dispersion used are applicable for low to medium viscosity silicones. If the silicone has a high viscosity, for example around 60,000 cst, the amounts of those components may be adjusted to 1.5% for the gel, and 0.225% for the stable dispersion. The adjustment for Sample 2 is 2.95% gel, and 0.35% dispersion. Formulations containing the higher amounts of silicone can be made using only the low to medium viscosity silicones.

The emulsions formed can be used as is, or easily added and mixed at room temperature in bases for car polishes, tyre shine products, shoe polish, furniture polish, antifoam products, conditioning shampoos, creams and lotions.

Example 7

A wax-containing end-use formulation emulsion was made using the gel composition made in Example 4. The emulsion was made using the ingredients shown in Table 2.

TABLE 2

| Ingredient | % by weight |
|---|---|
| Syncrowax ™ HGLC ($C_{18}$-$C_{35}$ acid triglyceride wax, ex Croda) | 30 |
| Gel composition | 2.5 |
| Water | 67.5 |
| Triethanolamine | qs |
| Total | 100 |

The wax was melted and the gel composition was added and mixed into it. The dispersion was dispersed in water and heated to 80° C. This mixture was then slowly added to the wax/gel mixture with further mixing taking place. The pH of the resultant formulation was adjusted to 6 to 7 using the triethanolamine and it was then cooled to ambient temperature.

Example 8

A thick cream tyre dressing end-use formulation emulsion was made using the gel composition made in Example 4 and the dispersion made in Example 1. The emulsion was made using the ingredients shown in Table 3.

TABLE 3

| Ingredient | % by weight |
|---|---|
| Silicone fluid, 350 cst | 2.5 |
| Silicone fluid, 60000 cst | 5 |
| Gel composition | 1.75 |
| Propylene glycol | 1 |
| Water | 91.5 |
| Triethanolamine | qs |
| Preservative | qs |
| Total | 100 |

The silicones, propylene glycol, gel composition and the dispersion were cold mixed. This mixture was then slowly added to the water with further mixing taking place. The pH of the resultant formulation was adjusted to 6 to 7 using the triethanolamine and was then cooled to ambient temperature. The formulation, when applied to tyres will provide premium shine.

Example 9

A black shoe polish end-use formulation emulsion was made using the gel composition made in Example 4 and the dispersion made in Example 1. The emulsion was made using the ingredients shown in Table 4.

TABLE 4

| Ingredient | % by weight |
|---|---|
| Syncrowax ™ HGLC ($C_{18}$-$C_{35}$ acid triglyceride wax, ex Croda) | 6 |
| Syncrowax ™ ERLC ($C_{18}$-$C_{35}$ acid glycol ester wax, ex Croda) | 2.6 |
| Paraffin wax | 8 |

TABLE 4-continued

| Ingredient | % by weight |
| --- | --- |
| Gel composition | 2.75 |
| Water | 80.65 |
| Triethanolamine | qs |
| Black colourant | qs |
| Total | 100 |

The waxes were melted and the gel composition was added and mixed into them. The dispersion was dispersed in water and heated to 90° C. This mixture was then slowly added to the wax/gel mixture with further mixing taking place. The pH of the resultant formulation was adjusted to neutral using the triethanolamine and it was then cooled to ambient temperature. The formulation, when applied to tyres will provide premium shine and black colour.

Example 10

A high gloss, cream car wax end-use formulation emulsion was made using the gel composition made in Example 1 and the dispersion made in Example 1. The emulsion was made using the ingredients shown in Table 5.

TABLE 5

| Ingredient | % by weight |
| --- | --- |
| Silicone fluid, 350 cst | 4 |
| Silicone fluid, 12500 cst | 2 |
| Silicone fluid, 60000 cst | 1 |
| Syncrowax ™ HGLC ($C_{18}$-$C_{36}$ acid triglyceride wax, ex Croda) | 4 |
| Gel composition | 2.75 |
| Water | 86.25 |
| Triethanolamine | qs |
| Preservative | qs |
| Total | 100 |

The silicones, wax, gel composition and the dispersion were mixed and then heated to 90° C. The dispersion was dispersed in water and heated to about 90° C. This mixture was then slowly added to the wax/gel mixture with further mixing taking place. The pH of the resultant formulation was adjusted to 6 to 7 using the triethanolamine and it was then cooled to ambient temperature.

Example 11

A solvent-free furniture polish end-use formulation emulsion was made using the gel composition made in Example 4 and the dispersion made in Example 1. The emulsion was made using the ingredients shown in Table 6.

TABLE 6

| Ingredient | % by weight |
| --- | --- |
| Silicone fluid, 350 cst | 2 |
| Silicone fluid, 60000 cst | 1 |
| Syncrowax ™ ERLC ($C_{18}$-$C_{36}$ acid glycol ester wax, ex Croda) | 4 |
| Gel composition | 2.25 |
| Water | 90.75 |
| Triethanolamine | qs |
| Preservative | qs |
| Total | 100 |

The silicones, wax, gel composition and the dispersion were mixed and then heated to 90° C. The dispersion was dispersed in water and heated to about 90° C. This mixture was then slowly added to the wax/gel mixture with further mixing taking place. The pH of the resultant formulation was adjusted to 6 to 7 using the triethanolamine and it was then cooled to ambient temperature.

Example 12

A shoe wipe end-use formulation emulsion was made using the gel composition made in Example 4. The emulsion was made using the ingredients shown in Table 7.

TABLE 7

| Ingredient | % by weight |
| --- | --- |
| Silicone fluid, 350 cst | 5 |
| Silicone fluid, 12500 cst | 5 |
| Syncrowax ™ HGLC ($C_{18}$-$C_{36}$ acid triglyceride wax, ex Croda) | 3.3 |
| Solan ™ E (PEG-75 lanolin, ex Croda) | 2 |
| Gel composition | 2 |
| Water | 82.7 |
| Triethanolamine | qs |
| Preservative | qs |
| Total | 100 |

The silicones and the gel composition were cold mixed. Water was slowly added to this mixture with further mixing taking place. The pH of the resultant formulation was adjusted to 6 to 7 using the triethanolamine.

Example 13

A leather wipe end-use formulation emulsion was made using the gel composition made in Example 4. The emulsion was made using the ingredients shown in Table 8.

TABLE 8

| Ingredient | % by weight |
| --- | --- |
| Silicone fluid, 350 cst | 3 |
| Silicone fluid, 12500 cst | 2 |
| Solan ™ E (PEG-75 lanolin, ex Croda) | 3 |
| Gel composition | 1.5 |
| Water | 90.5 |
| Triethanolamine | qs |
| Preservative | qs |
| Total | 100 |

The silicones and the gel composition were cold mixed. Water was slowly added to this mixture further mixing taking place. The pH of the resultant formulation was adjusted to 6 to 7 using the triethanolamine.

Example 14

An antistatic furniture wipe end-use formulation emulsion was made using the gel composition made in Example 4. The emulsion was made using the ingredients shown in Table 9.

TABLE 9

| Ingredient | % by weight |
| --- | --- |
| Silicone fluid, 350 cst | 2 |
| Silicone fluid, 60000 cst | 1 |

TABLE 9-continued

| Ingredient | % by weight |
|---|---|
| Syncrowax ™ HGLC ($C_{18}$-$C_{36}$ acid triglyceride wax, ex Croda) | 2 |
| Crodastat ™ 300(cationic antistatic agent, ex Croda) | 0.3 |
| Gel composition | 1.6 |
| Water | 93.1 |
| Triethanolamine | qs |
| Preservative | qs |
| Total | 100 |

The silicones and the gel composition were cold mixed. The wax and antistatic agent were then added to the mixture with further mixing. Water was slowly added to this mixture further mixing taking place. The pH of the resultant formulation was adjusted to 6 to 7 using the triethanolamine.

Example 15

A number of wipe end-use formulations were made using the gel composition made in Example 4. The formulations were made using the % by weight of the ingredients shown in Table 10 for application to wipe substrates.

TABLE 10

| Ingredient | A | B | C | D | E |
|---|---|---|---|---|---|
| Gel composition | 5.0 | 5.0 | 5.0 | 5.0 | 5.0 |
| Moist 24 (*Imperata cylindrica* extract) | 2.0 | | | | |
| MATRIXYL ™ 3000 (Synthetic pentapeptide, ex Sederma) | | 2.0 | | | |
| Prostearyl 15 | | | 2.0 | | |
| Petrolatum | | | | 3.0 | |
| Silicone 200 | | | | 6.0 | |
| CRODAMOL ™ GTCC (caprylic/capric triglyceride, ex Croda) | | | 5.0 | 5.0 | 2.0 |
| Insect repellent Nova | | | | | 5.0 |
| PHENOVA ™ (preservative composition, ex Crodarom) | 0.5 | 0.5 | 0.5 | 0.5 | 0.5 |
| Perfume | | | | | 0.3 |
| Water | 92.5 | 92.5 | 87.5 | 80.5 | 87.2 |
| Triethanolamine | qs | qs | qs | qs | qs |
| Total | 100 | 100 | 100 | 100 | 100 |

The wipe formulations are identified as follows:
A=facial moisturising wipe, B=facial anti-wrinkle wipe, C=facial make-up remover wipe, D=baby wipe, and E=mosquito repellent wipe.

Example 16

An emulsification system according to the present invention was prepared using the dispersion made in Example 4 together with the ingredients shown in Table 11, and in the proportions shown therein.

TABLE 11

| Ingredient | Weight % |
|---|---|
| CRODAMOL ™ GTCC (caprylic/capric triglyceride, ex Croda) | 36 |
| CITHROL ™ EGMS 3127 (glycol stearate, ex Croda) | 12 |
| CITHROL ™ GMS 0400 (glyceryl stearate, ex Croda) | 3 |
| VOLPO ™ S2 (steareth-2, ex Croda) | 3 |
| VOLPO ™ S20 (steareth-20, ex Croda) | 3 |
| Dispersion | 3 |
| GLYCEROX ™ HE (PEG-7 glyceryl cocoate, ex Croda) | 10 |
| Water | 30 |

The CRODAMOL GTCC (caprylic/capric triglyceride, ex-Croda) was heated in a suitable vessel equipped with a paddle stirrer. The stirrer was operated throughout the preparation of the emulsification system. The temperature to which the oil was heated was a temperature of at least the highest melting point of the solid non-ionic surfactants, following which CITHROL EGMS 3127 (glycol stearate, ex Croda), CITHROL GMS 0400 (glyceryl stearate, ex Croda), VOLPO S2 (steareth-2, ex Croda) and VOLPO S20 (steareth-20, ex Croda) were added and homogeneously dispersed in the oil. The temperature of the mixture was then adjusted to about 40 to 45° C. The GLYCEROX HE (PEG-7 glyceryl cocoate, ex Croda) was then added to the mixture. The temperature of the mixture was then adjusted to a maximum of 30° C., following which the dispersion of Example 4 was added. The mixture was mixed for a period to ensure the dispersion was homogeneously spread throughout the mixture to produce a smooth mixture. Water was then added to the vessel and mixed at a rate that avoids bubble formation. As the water was added, phase inversion occurred to form an oil-in-water emulsion. The emulsion was stable after 3 months at 43° C. and to three freeze-thaw cycles. The emulsification system was an easy to handle light white paste.

Example 17

A hydrating end-use formulation was prepared using the emulsification system made in Example 16, and the ingredients are shown in Table 12.

TABLE 12

| Ingredient | Weight % |
|---|---|
| Emulsification system | 15 |
| PHENOVA ™ (preservative composition, ex Crodarom) | 0.5 |
| Water - deionised | 84.5 |
| Triethanolamine | qs |
| Total | 100 |

The water and preservative were added slowly to the emulsification system with moderate mixing until homogeneous. The mixture was then mixed for a further 15 minutes minimum at a high rate, but without causing aeration. The final pH of the formulation was adjusted to 6 to 6.5. The emulsion was mixed until homogeneous. The final formulation had a viscosity of 15,000 cPs and was stable after 3 months at 43° C. and to three freeze-thaw cycles. The formulation was light to the touch, and easily absorbed on the skin leaving a light, non-tacky feel.

Example 18

A barrier cream end-use formulation was prepared using lanolin and the emulsification system made in Example 16, and the ingredients are shown in Table 13.

TABLE 13

| Ingredient | Weight % |
|---|---|
| Emulsification system | 30 |
| PHENOVA ™ (preservative composition, ex Crodarom) | 0.5 |
| MEDILAN ™ (lanolin, ex Croda) | 10 |
| CRODURET ™ 7 (PEG-7 hydrogenated caster oil, ex-Croda) | 2 |

TABLE 13-continued

| Ingredient | Weight % |
| --- | --- |
| Water - deionised and slightly alkaline | 57.5 |
| Triethanolamine | qs |
| Total | 100 |

The ethoxylated castor oil, preservative and lanolin were added to the emulsification system and mixed until homogeneous and emulsified. A coarse water-in-oil emulsion was formed. Water was then added slowly with mixing at moderate to high speed until all the water had been emulsified. The emulsion inverted to a smooth and shiny oil-in-water emulsion. The final pH of the formulation was adjusted to 6 to 6.5. The emulsion was mixed until homogeneous. The final formulation had a viscosity of 44,000 cPs and was stable after 3 months at 43° C. and to three freeze-thaw cycles. The formulation did not have the greasiness and tackiness normally associated with lanolin formulations.

Example 19

A cleansing milk make-up remover end-use formulation was prepared using the emulsification system made in Example 16, and the ingredients are shown in Table 14.

TABLE 14

| Ingredient | Weight % |
| --- | --- |
| Emulsification system | 15 |
| PHENOVA ™ (preservative composition, ex Crodarom) | 0.5 |
| CRODAMOL ™ PMP (PPG-2 myristyl ether propionate, ex Croda). | 5 |
| Glycerin | 5 |
| Mineral oil | 2 |
| Cyclomethicone | 1.5 |
| Water - deionised | qs to 100 |
| Triethanolamine | qs |
| Total | 100 |

The ingredients were added slowly to the emulsification system with moderate mixing until homogeneous and emulsified. The mixture was then mixed for a further 15 minutes minimum at a high rate, but without causing aeration. The final pH of the formulation was adjusted to 6 to 6.5. The emulsion was mixed until homogeneous. The final formulation had a viscosity of 11,000 cPs and was stable after 3 months at 43° C. and to three freeze-thaw cycles. The formulation easily wiped out water-resistant make up without leaving a greasy after-feel.

Example 20

A hair conditioner end-use formulation was prepared using the emulsification system made in Example 18, the dispersion made in Example 1, and the ingredients are shown in Table 15.

TABLE 15

| Ingredient | Weight % |
| --- | --- |
| Emulsification system | 15 |
| PHENOVA ™ (preservative composition, ex Crodarom) | 0.5 |
| Dimethiconol | 0.5 |

TABLE 15-continued

| Ingredient | Weight % |
| --- | --- |
| Water - deionised (pH 8 to 8.5 neutralised with NaOH) | qs to 100 |
| LUSTREPLEX ™ (polyquaternium-70 dipropylene glycol, ex Croda) | 2 |
| OPTASENSE ™ CP7 (cationic polymer, ex Croda) | 2 |
| Dispersion | 0.55 |
| Total | 100 |

The dimethiconol, water and preservative were added slowly to the emulsification system with moderate mixing until homogeneous and emulsified. The pH of the mixture was then adjusted to about 7.5. The polyquarternium and the cationic polymer were then added with mixing. The dispersion from Example 1 was then added with mixing until homogeneous. The final pH of the formulation was adjusted to 5.5 to 6. The emulsion was mixed until homogeneous. The final formulation had a viscosity of 32,000 cPs and was stable after 3 months at 43° C. and to three freeze-thaw cycles. The formulation produced a light-weight hair conditioner with outstanding shine, compatibility and smoothness, providing hair with volume and manageability.

Example 21

A whitening lotion with sunscreen protection end-use formulation was prepared using the emulsification system made in Example 16, and the ingredients are shown in Table 16.

TABLE 16

| Ingredient | Weight % |
| --- | --- |
| Emulsification system | 15 |
| PHENOVA ™ (preservative composition, ex Crodarom) | 0.5 |
| LUMISKIN ™ (diacetyl boldine in caprylic/capric triglycerides, ex Sederma) | 1 |
| Menthyl anthranilate | 5 |
| Octocrylene | 8 |
| Octyl salicylate | 5 |
| Octyl methoxycinnamate | 7.5 |
| Perfume | 0.2 |
| Water - deionised | qs to 100 |
| Triethanolamine | qs |
| Total | 100 |

The ingredients, apart from the triethanolamine, were added slowly to the emulsification system according to the invention with moderate mixing until homogeneous. The mixture was then mixed for a further 15 minutes minimum at a high rate, but without causing aeration. The final pH of the formulation was adjusted to 6 to 6.5. The emulsion was mixed until homogeneous. The final formulation had a viscosity of 16,000 cPs and was stable after 3 months at 43° C. and to three freeze-thaw cycles. The formulation was unusually light and easily absorbed while leaving a soft cushiony feel on the skin.

Example 22

A night renewal moisturiser end-use formulation for mature skins was prepared using the emulsification system made in Example 16, and the ingredients are shown in Table 17.

TABLE 17

| Ingredient | Weight % |
| --- | --- |
| Emulsification system | 20 |
| PHENOVA ™ (preservative composition, ex Crodarom) | 0.5 |
| CRODAMOL ™ TN (tridecyl isononanate, ex Croda) | 5 |
| CRODAMOL ™ AB ($C_{12}$ to $C_{15}$ alkyl benzoate, ex-Croda) | 2 |
| CRODADERM ™ S (sucrose polysoyate, ex-Croda) | 0.5 |
| SUPERMOL ™ S (pentaerythrityl stearate/caprate/caprylate/adipate, ex-Croda) | 1 |
| CHRONODYN ™ (*Euglena gracilis* extract in glycerine, ex-Sederma) (skin energiser) | 3 |
| Perfume | 0.2 |
| Moist 24 (*Imperata cylindrica* extract) | 1 |
| Vitamin E WS | 0.1 |
| Water - deionised | qs to 100 |
| Triethanolamine | qs |
| Total | 100 |

The ingredients, except for triethanolamine, were added slowly to the emulsification system with moderate mixing until homogeneous and emulsified. The mixture was then mixed for a further 15 minutes minimum at a high rate, but without causing aeration. The final pH of the formulation was adjusted to 6 to 6.5. The emulsion was mixed until homogeneous. The final formulation had a viscosity of 22,000 cPs and was stable after 3 months at 43° C. and to three freeze-thaw cycles.

Example 23

A thick cream base end-use formulation was prepared using the emulsification system made in Example 16, and the ingredients are shown in Table 18.

TABLE 18

| Ingredient | Weight % |
| --- | --- |
| Emulsification system | 35 |
| PHENOVA ™ (preservative composition, ex Crodarom) | 0.5 |
| CRODAMOL ™ STS (PPG-3 benzyl ether myristate, ex Croda) | 6 |
| White petrolatum | 3 |
| Water - deionised | qs to 100 |
| Triethanolamine | qs |
| Total | 100 |

The ingredients, except the triethanolamine, were added slowly to the emulsification system with moderate mixing until homogeneous and emulsified. The mixture was then mixed for a further 15 minutes minimum at a high rate, but without causing aeration. The final pH of the formulation was adjusted to 6 to 6.5. The emulsion was mixed until homogeneous. The final formulation had a viscosity of 35,000 cPs and was stable after 3 months at 43° C. and to three freeze-thaw cycles.

Example 24

An anti-acne cream end-use formulation was prepared using the emulsification system made in Example 16, and the ingredients are shown in Table 19.

TABLE 19

| Ingredient | Weight % |
| --- | --- |
| Emulsification system | 30 |
| PHENOVA ™ (preservative composition, ex Crodarom) | 0.5 |
| AC.NET ™ (anti-acne treatment, ex Sederma) | 3 |
| Witchhazel distillate | 0.1 |
| White tea (ex Crodarom SAS) | 0.1 |
| Perfume | 0.1 |
| Water - deionised (pH 8-8.5) | qs to 100 |
| Triethanolamine | qs |
| Total | 100 |

Water was added slowly to the emulsification system with moderate mixing until homogeneous. The remaining ingredients, except for the triethanolamine, were added. The mixture was then mixed for a further 15 minutes minimum at a high rate, but without causing aeration. The final pH of the formulation was adjusted to 6 to 6.5. The emulsion was mixed until homogeneous. The formulation imparted a light, non-greasy feel and a smooth dry-down feel to skin. The anti-acne component, AC.Net™, prevents excessive oil production, cell proliferation, inflammation and bacterial growth.

Example 25

An intensive moisturising cream end-use formulation was prepared using the emulsification system made in Example 16, and the ingredients are shown in Table 20.

TABLE 20

| Ingredient | Weight % |
| --- | --- |
| Emulsification system | 30 |
| PHENOVA ™ (preservative composition, ex Crodarom) | 0.5 |
| Moist 24 (*Imperata cylindrica* extract) | 3 |
| VOLPO ™ G26 (glycereth-26, ex Croda) | 2 |
| Perfume | 0.1 |
| Water - deionised | qs to 100 |
| Triethanolamine | qs |
| Total | 100 |

Water was added slowly to the emulsification system with moderate mixing until homogeneous. The remaining ingredients, except for the triethanolamine, were added. The mixture was then mixed for a further 15 minutes minimum at a high rate, but without causing aeration. The final pH of the formulation was adjusted to 6 to 6.5. The emulsion was mixed until homogeneous. The formulation provided long-lasting moisturizing effect to the skin with excellent aesthetics and sensory properties.

Example 26

A skin restructuring age control cream end-use formulation was prepared using the emulsification system made in Example 16, and the ingredients are shown in Table 21.

TABLE 21

| Ingredient | Weight % |
| --- | --- |
| Emulsification system | 30 |
| PHENOVA ™ (preservative composition, ex Crodarom) | 0.5 |
| MATRIXYL ™ 3000 (synthetic pentapeptide, ex Sederma) | 3 |

TABLE 21-continued

| Ingredient | Weight % |
| --- | --- |
| CRODAMOL ™ TN (tridecyl isononanate, ex Croda) | 3 |
| Perfume | 0.1 |
| Water - deionised | qs to 100 |
| Triethanolamine | qs |
| Total | 100 |

Water was added slowly to the emulsification system according to the invention with moderate mixing until homogeneous. The remaining ingredients, except for the triethanolamine, were added. The mixture was then mixed for a further 15 minutes minimum at a high rate, but without causing aeration. The final pH of the formulation was adjusted to 6 to 6.5. The emulsion was mixed until homogeneous. The formulation provided a vehicle for delivery of the synthetic pentapeptide active with excellent aesthetics and sensory properties.

Example 27

A dispersion was made by mixing, using a propeller stirrer at ambient temperature, the following ingredients:
7% by weight of Crester™ PR (polyglyceryl-3 polyricinoleate, ex Croda);
49% by weight of CRODAMOL GTCC (caprylic/capric triglyceride, ex Croda);
14% by weight of CRODAMOLLIENT TMC (tri-PPG-3 myristyl ether citrate, ex Croda; and
30% by weight of Acrylates\C10-30 Alkyl Acrylate Crosspolymer.

The liquid phase ingredients were initially mixed together, and then the carboxylic acid polymer, which is in powder form, was slowly introduced with continued stirring until a homogeneous dispersion was obtained.

A gel composition was made by mixing 16% by weight of the dispersion with 9.3% by weight of Crill™ 4 (sorbitan oleate, ex Croda), 67.3% by weight of Glycerox™ HE (PEG-7 glyceryl cocoate (ex Croda)), and 7.4% by weight of water.

Example 28

A dispersion and gel were made as described in Example 27 except that light mineral oil was used instead of caprylic/capric triglyceride.

Example 29

The dispersions and gels produced in Examples 27 and 28 were particularly suitable for use in thickening surfactant-based formulations such as shampoos and body washes, and in foaming emulsions. One particular use is as part of an emulsifier system for explosives as shown in Table 22.

TABLE 22

| Ingredient | Weight % |
| --- | --- |
| Gel composition | 26.7 |
| Crill ™ 4 (sorbitan oleate, ex Croda) | 66.7 |
| Oleic acid | 6.6 |
| Total | 100 |

It is to be noted that the end-use formulations described herein were all prepared using cold processing, i.e. at ambient temperature (23° C.).

The above examples illustrate the improved properties of a dispersion, gel, emulsification system and emulsion according to the present invention.

The invention claimed is:

1. A dispersion of polymer particles, consisting of greater than 5% by weight of high molecular weight polycarboxy or polycarboxylic acid polymer particles having a molecular weight of greater than 10,000 and no more than 3,000,000 dispersed in an organic medium having a non-ionic surfactant and 8 wt. % to 18 wt. % of a propoxylated ester having a Hansen and Beerbower solubility parameter in the range of 15 to 25;
wherein the dispersion consists of the polycarboxy or polycarboxylic acid polymer particles, the non-ionic surfactant, and the propoxylated ester.

2. The dispersion of polymer particles according to claim 1, comprising 25 wt. % to 50 wt. % of the high molecular weight polycarboxy or polycarboxylic acid polymer particles.

3. The dispersion of polymer particles according to claim 1, comprising 20-80 wt. % of the organic medium, said organic medium having dispersed therein greater than 10 wt. % of the high molecular weight polycarboxy or polycarboxylic acid polymer particles, each amount based on the total weight of the dispersion.

4. The dispersion of claim 1, wherein:
i) the propoxylated ester is di-PPG-3 myristyl ether adipate or tri-PPG-3 myristyl ether citrate; and/or
ii) the non-ionic surfactant is a sorbitan ester.

5. The dispersion of claim 1, wherein the polycarboxy or polycarboxylic acid polymer particles are not neutralized.

6. The dispersion of claim 5, comprising 30 wt. % to 50 wt. % of said high molecular weight polycarboxy or polycarboxylic acid polymer particles.

* * * * *